(12) United States Patent  (10) Patent No.:  US 6,639,671 B1
Liu                        (45) Date of Patent:     Oct. 28, 2003

(54) WIDE-RANGE PARTICLE COUNTER

(75) Inventor: Benjamin Y. H. Liu, North Oaks, MN (US)

(73) Assignee: MSP Corporation, Minneapolis, MN (US)

( * ) Notice: Subject to any disclaimer, the term of this patent is extended or adjusted under 35 U.S.C. 154(b) by 0 days.

(21) Appl. No.: 10/087,491

(22) Filed: Mar. 1, 2002

(51) Int. Cl.⁷ .............................................. G01N 15/02
(52) U.S. Cl. ...................... 356/336; 356/343; 356/38; 356/37; 250/574; 73/28.01
(58) Field of Search ................................ 356/335–343, 356/37–38; 73/28.01–28.05, 863.22, 865.5, 865.6; 422/73, 110; 241/19, 23; 250/574, 575, 304

(56) References Cited

U.S. PATENT DOCUMENTS

| 2,732,753 A | 1/1956 | O'Konski | 88/14 |
|---|---|---|---|
| 2,816,479 A | 12/1957 | Sloan | 88/14 |
| 2,920,525 A | 12/1960 | Appel et al. | 88/14 |
| 3,248,551 A | 4/1966 | Frommer | 250/218 |
| 3,406,289 A | 10/1968 | Schleusener | 250/217 |
| 3,614,231 A | 10/1971 | Shaw | 356/37 |
| 3,694,085 A | 9/1972 | Rich | 356/37 |
| 3,721,014 A * | 3/1973 | Voelskow | 34/10 |
| 3,806,248 A | 4/1974 | Sinclair | 356/37 |
| 4,178,796 A * | 12/1979 | Zwicker et al. | 73/61.4 |
| 4,449,816 A | 5/1984 | Kohsaka et al. | 356/37 |
| 4,571,079 A | 2/1986 | Knollenberg | 356/336 |
| 4,761,074 A * | 8/1988 | Kohsaka et al. | 356/336 |
| 4,790,650 A | 12/1988 | Keady | 356/37 |
| 4,794,086 A * | 12/1988 | Kasper et al. | 356/336 |
| 4,844,349 A * | 7/1989 | Kanda et al. | 214/19 |
| 4,893,928 A | 1/1990 | Knollenberg | 356/336 |
| 5,084,629 A | 1/1992 | Petralli | 250/573 |
| 5,247,842 A * | 9/1993 | Kaufman et al. | 73/865.5 |
| 5,374,396 A * | 12/1994 | Blackford et al. | 356/335 |
| 5,596,136 A | 1/1997 | Flagan et al. | 73/28.04 |
| 5,659,388 A * | 8/1997 | Scheer et al. | 356/37 |
| 5,922,976 A * | 7/1999 | Russell et al. | 73/865.5 |
| 5,932,818 A * | 8/1999 | Novick et al. | 73/863.22 |
| 6,003,389 A * | 12/1999 | Flagan et al. | 73/865.5 |
| 6,230,572 B1 | 5/2001 | Pui et al. | 73/863.21 |
| 6,435,043 B1 * | 8/2002 | Ferguson et al. | 73/865.5 |
| 6,469,780 B1 * | 10/2002 | McDermott et al. | 356/37 |

OTHER PUBLICATIONS

"A Submicron Aerosol Standard and the Primary, Absolute Calibration of the Condensation Nuclei Counter," Benjamin Y.H. Lie, David Y.H. Pui, *Journal of Colloid and Interface Science*, vol. 47, No. 1, Apr. 1974.

"Aerosol Classification by Electric Mobility: Apparatus, Theory, and Applications," *Journal of Aerosol Science*, 1975 pp. 443–451, W.O. Knutson and K.T. Whitby.

"Design and Testing of an Aersol/Sheath Inlet for High Resolution Measurements with a DMA," Da–Ren Chen, David U.H. Piu, George W. Mulholland, and Marco Fernandez, *Journal of Aerosol Science*, vol. 30, No. 8, pp. 983–999, 1999.

* cited by examiner

*Primary Examiner*—Frank G. Font
*Assistant Examiner*—Sang H. Nguyen
(74) *Attorney, Agent, or Firm*—Westman, Champlin & Kelly, P.A.

(57) ABSTRACT

A wide range particle counter has sections which separately detect coarse and fine particles in an aerosol. The coarse particles are counted and sized in an optical particle counter. The fine particles are classified with a differential mobility analyzer to determine size and then passed through a vaporizer and condenser and also counted. Using the different sections permits counting and measuring a wide range of particle size in a single instrument with high accuracy and reliability.

37 Claims, 5 Drawing Sheets

WIDE-RANGE PARTICLE COUNTER

BACKGROUND OF THE INVENTION

The present invention relates to a method and apparatus for measuring the size distribution of aerosols over a wide particle size range. Specifically, the invention relates to the measurement of particles suspended in a gas, which is referred to as an aerosol. The most common carrier gas is air, but other gases, such as nitrogen, helium, argon, $CO_2$, and other gases, may also be the media for particle suspension. The particles can be solid, liquid, or a mixture of both.

In the ambient atmosphere, particles may exist over a size range from about 2 nanometers (nm) to over 50,000 nm in diameter, with particles in the 10 nm to 10,000 nm range being the most important from a health and safety standpoint. No single device currently exists that can measure particles over this range. The wide-range particle counter (WPC) described herein makes this possible.

Particle counters now available have a limited operable range of sizes, and several different particle counters are needed to properly analyze aerosols.

Aerosols occur both in nature and in the human environment. They are important in scientific research and in technical applications. Aerosol particles in the atmosphere can scatter light and affect atmospheric visibility. When inhaled, the suspended particles can deposit in the lungs to cause potential health effects in humans. Aerosol particles often need to be measured so the sources of the particles can be controlled or precautions taken if the sources cannot be controlled.

Aerosols are also generated on purpose for scientific and technical applications. In laboratory studies, for instance, aerosols with controlled size distribution are needed to test filters and other particle collectors to determine their efficiency. In medical applications, drug compounds are frequently generated in aerosol form for delivery to the lungs for disease treatment. The particle size distribution is important because particle size determines the specific regions of the lungs where the inhaled particles will deposit, hence the effectiveness and efficacy of the inhaled drugs. In all cases in this specification, a gas containing suspended particles shall be referred to as an aerosol, with no limitation being made as to the chemical nature of the particles and that of the gas, and their respective physical states.

One of the most widely used aerosol-measuring instruments presently is the optical particle counter (OPC) first described in U.S. Pat. No. 2,732,753 (O'Konski). In an OPC, the aerosol is passed through a beam of light to cause optical scattering. The scattered light signal from each particle is then detected and related to particle size. The OPC is capable of detecting particles to a lower size limit of about 100 nm in diameter, with some special OPCs having been designed to detect particles as small as 60 nm in diameter or a characteristic dimension.

Another particle-measuring instrument is the condensation nucleus counter (CNC), also referred to as a condensation particle counter. The most widely used CNC is that based on U.S. Pat. No. 4,790,650 (Keady). In this CNC, the aerosol is first saturated with the vapor of a working fluid at an elevated temperature. A typical working fluid is butyl alcohol, and a typical saturator temperature is 35° C. The vapor-laden aerosol then passes through a condenser, typically kept at 5° C. to cool the gas and cause the vapor to condense on particles to form droplets. The droplets are then counted by optical scattering, as in a conventional OPC. The CNC is capable of detecting particles below the lower size limit of the OPC, since droplets formed by vapor condensation are considerably larger than the particles themselves, thus making them easier to detector by light scattering.

Since a CNC is only capable of counting particles, but not measuring the particle size, a CNC must be combined with a size-analyzing device, such as a mobility analyzer, in order to both determine the size and the particles count. A differential mobility analyzer (DMA) is usually used for size determination. The DMA method of size classification is based on the electrical mobility of singly charged particles, i.e. particles carrying a single electron unit of charge. Liu and Pui (1974) and Knutson and Whitby (1975) were the developers of the DMA for this application. The publications explaining this DMA method are: "A Submicron Aerosol Standard and the Primary, Absolute Calibration of the Condensation Nuclei Counter," Benjamin Y. H. Liu, David Y. H. Pui, *Journal of Colloid and Interface Science*, vol. 47, No. 1, Apr. 1974; and "Aerosol Classification by Electric Mobility: Apparatus, Theory, and Applications," *Journal of Aerosol Science*, 1975 pp. 443–451, W. O. Knutson and K. T. Whitby.

Recent improvements in the DMA are described in the article "Design and Testing of an Aerosol/Sheath Inlet for High Resolution Measurements with a DMA," Da-Ren Chen, David Y. H. Pui, George W. Mulholland, and Marco Fernandez, *Journal of Aerosol Science*, Vol. 30, No. 8, pp. 983–999, 1999 by Chen et al (1995). The development of the nano-DMA for particle measurement below 50 nm in particle diameter is disclosed by Pui et al in U.S. Pat. No. 6,230,572 B1. These recent developments further improved the accuracy and range of the DMA devices.

The DMA method of size classification relies on the fact that the electrical mobility of a singly charged particle is inversely related to particle size. A polydisburse aerosol containing singly charged particles over a range of sizes can be classified according to size in an electric field and produce a nearly monodisburse aerosol within a narrow range of electrical mobilities and thus the produced aerosol contains particles of substantially the same size. The classified aerosol can then be counted by a CNC. The DMA is generally limited to particles smaller than about 500 nm in diameter.

All aerosol-measuring instruments have certain inherent size limits. In the case of the DMA, the limit is due to the low electrical mobility of large particles. As the particle size increases, the electrical voltage needed to classify the particle by electrical mobility also increases. At the usual flow rate used in differential mobility analysis, voltages as high as 10,000 Volts may be needed to classify particles at a diameter of 500 nm. For this reason, mobility analysis is seldom used beyond an upper size limit of about 500 nm.

On the other hand, the OPC is limited in the particle size it can satisfactorily detect due to the scattered light signal from a particle generally decreasing with decreasing particle size. Below about 100 nm, the scattered light signal begins to enter the so-called Rayleigh scattering regime, where the signal varies approximately as the sixth power of particle size. A factor-of-two reduction in particle size would thus lead to approximately a 64-fold reduction in the scattered light signal. Detecting small particles below 100 nm becomes increasingly more difficult, even when using a high-powered lasers as light sources, collecting optics with a high numerical aperture, and sensitive photo-detectors. Although optical particle counters have been designed to detect particles as small as 60 nm in diameter, the equipment needed is generally large and expensive. For this reason, high sensitivity optical particle counters are not widely used.

In principle, optical particle counters can be further improved to detect particles smaller than 60 nm. With further advance, even smaller particles may be detectable. However, advances in optical particle counting technology have not made the technology more useful for aerosol measurement over a wide size range. Designers of optical particle counters have not recognized the issues related to wide range particle counting and the special requirements that must be met in order to measure particles over a wide size range. A requirement that is illustrated with the following example.

In the ambient atmosphere, the aerosol size distribution generally follows Junge's law, which states that the concentration of aerosol particles larger than a certain size is inversely proportional to the $3^{rd}$ power of particle size. If the atmospheric particle concentration larger than 50 nm is, say 30,000 particles per cc, then the concentration of particles larger than 500 nm would be a factor of 1,000 lower, or on the order of 30 particles per cc. For particles larger than 5,000 nm, the concentration would be a million times lower, or on the order of 0.03 particles per cc.

The sharply declining concentration of large particles in the atmosphere indicates that even if a single detector is developed that can detect particles over a wide size range, say, from 50 nm to 10,000 nm in diameter, the detector, when operated at a specific sampling flow rate, would result in very high particle count rates in the small particle range, and a very low count rate in the large particle range.

For instance, at a sampling flow rate of 1 liter per minute (1 pm), i.e. 1,000 cc per minute, each minute would give rise to 30,000,000 particles in the 50 nm to 500 nm diameter range that need to be counted. Such a count rate is generally too high and would exceed the count rate limitation of the current optical counter technology. On the other hand, each minute of sampling by the detector would only yield 30 counts for particles in the greater than 5,000 nm range. Such a particle count is usually too low for statistically accurate purposes.

In order to count atmospheric fine particles in the 50 nm to 500 nm range at a more reasonable rate, the flow rate of the detector may be reduced to, say, 0.1 lpm so that only 3,000,000 particles need to be counted each minute. At such a sampling flow rate, the detector would yield only 3 particle counts in the greater than 5,000 nm range each minute, thus worsening the statistical accuracy of the large particle count. On the other hand, if the sampling flow rate is increased to, say, 10 pm so that 300 particles in the greater than 5,000 nm range can be counted each minute to improve the statistical counting accuracy for large particles, 300,000,000 particles would need to be counted in the 50 nm to 500 nm range, thus worsening the count-rate requirement of the counter for fine particles.

This example illustrates why the OPC is unable to measure aerosols over a wide size range, and why the conventional OPC by itself is inherently incapable of making such measurements with accuracy over the entire particle size range of interest in aerosols.

SUMMARY OF THE INVENTION

The present invention is a single measuring instrument built on a common chasis or a single platform, using multiple sensors provided with appropriate flow rates to detect and measure aerosol particles over a wide size range, typically from 10 nm to 10,000 nm in diameter, and greater for example, from 2 nm to 50,000 nm. Instrument sections measuring the 10 nm to 10,000 nm particle size are termed wide-range particle counters (WPC) and the 2 nm to 50,000 nm range instrument sections are termed ultra-wide range, particle counters (UWPC). These instruments make it possible to carry out measurements that are not possible with currently available instrumentation.

The WPC described in this specification is based on the novel combination of multiple sensors or detectors that combine optical detection with electrical mobility analysis to form a single device covering a wide particle size range. Each sensor is optimized in terms of particle measurement range, aerosol flow rate, reduced particle loss in sampling lines, and optical and electrical designs.

The measuring instrument of the present invention is simple in design and yet capable of performing the measurement automatically over a wide size range.

The lower limit is preferably 2 nm to 20 nm, and the upper limit can be anywhere between 5,000 nm and 50,000 nm.

The instrument includes controls for controlling operating parameters in order to insure reliable instrument operation, accuracy of measurement, and ease of use.

The number of sensors, flowmeters, pumps, and other components are minimized so that a rather complicated instrument like the WPC can be simplified and manufactured at a reasonable cost.

The resulting instrument described herein is estimated to weigh less than 35 lbs., making the device quite portable and convenient to use.

DETAILED DESCRIPTION OF THE PREFERRED EMBODIMENTS

Figure 1:
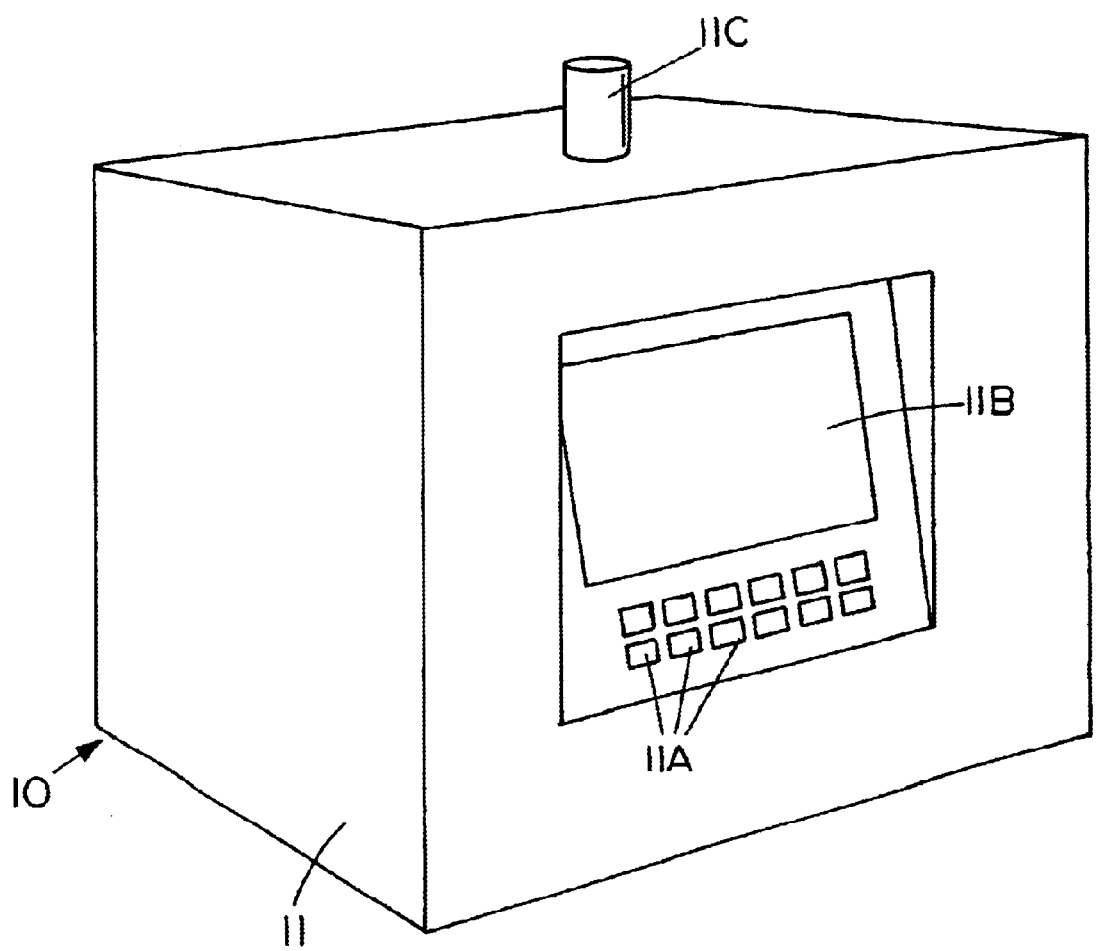
FIG. 1 is a schematic representation of a wide range particle counter instrument showing a chassis or housing.
Figure 2:
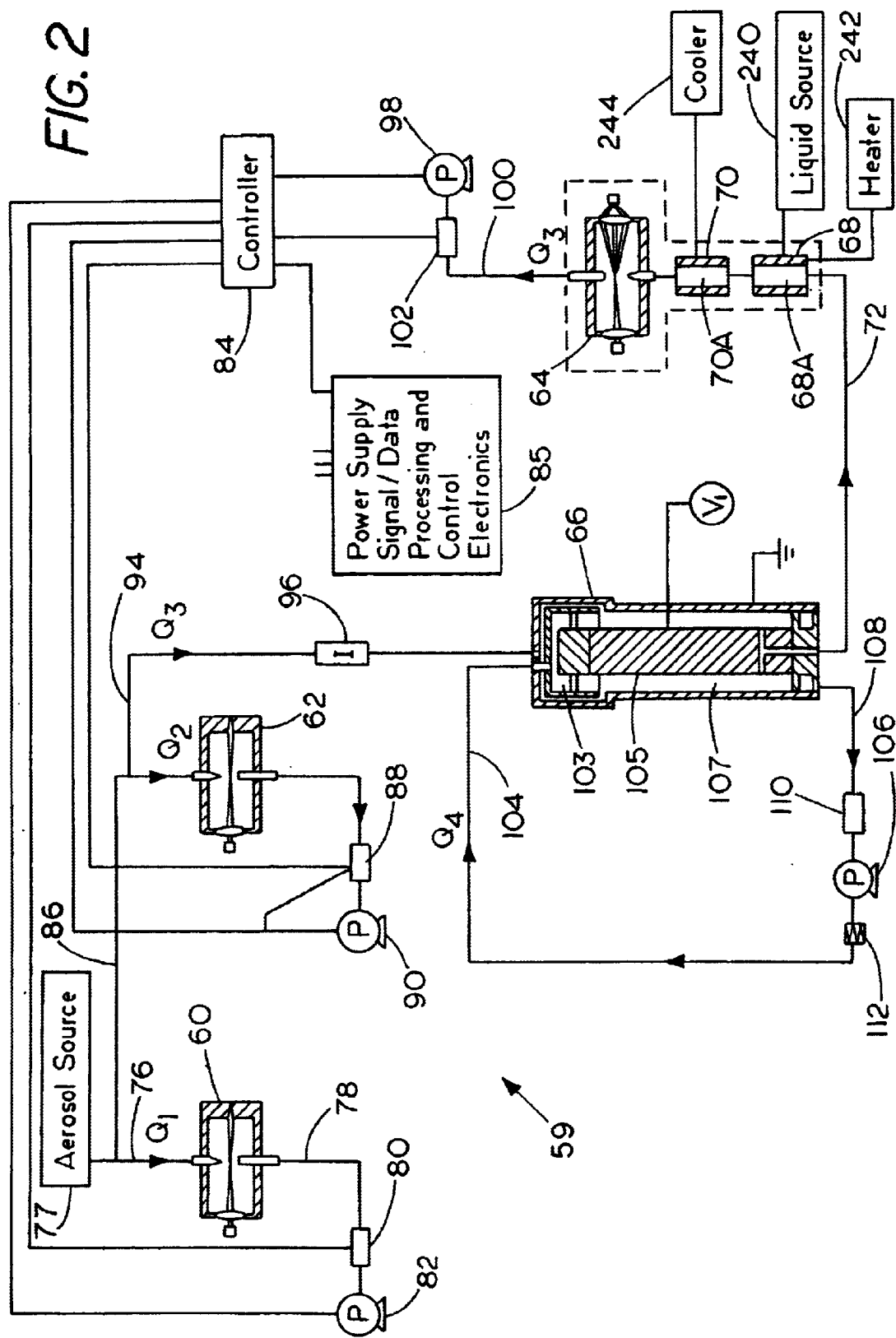
FIG. 2 is a schematic diagram of a second embodiment of the invention using a different sensor arrangement.

In FIG. 1, a typical wide particle counter 10 is illustrated. The components shown in FIGS. 1 and 2 are on a chassis or platform 11 that houses the components. The chassis platform provide a support structure for the components. The controls that are described later can receive operator inputs from control or function buttons 11A. Display screen 11B is provided to display messages or readouts from an internal processor or computer forming the controls.

An inlet nozzle or tube 11C is also shown and leads to the internal lines and counters.

Figure 1A:
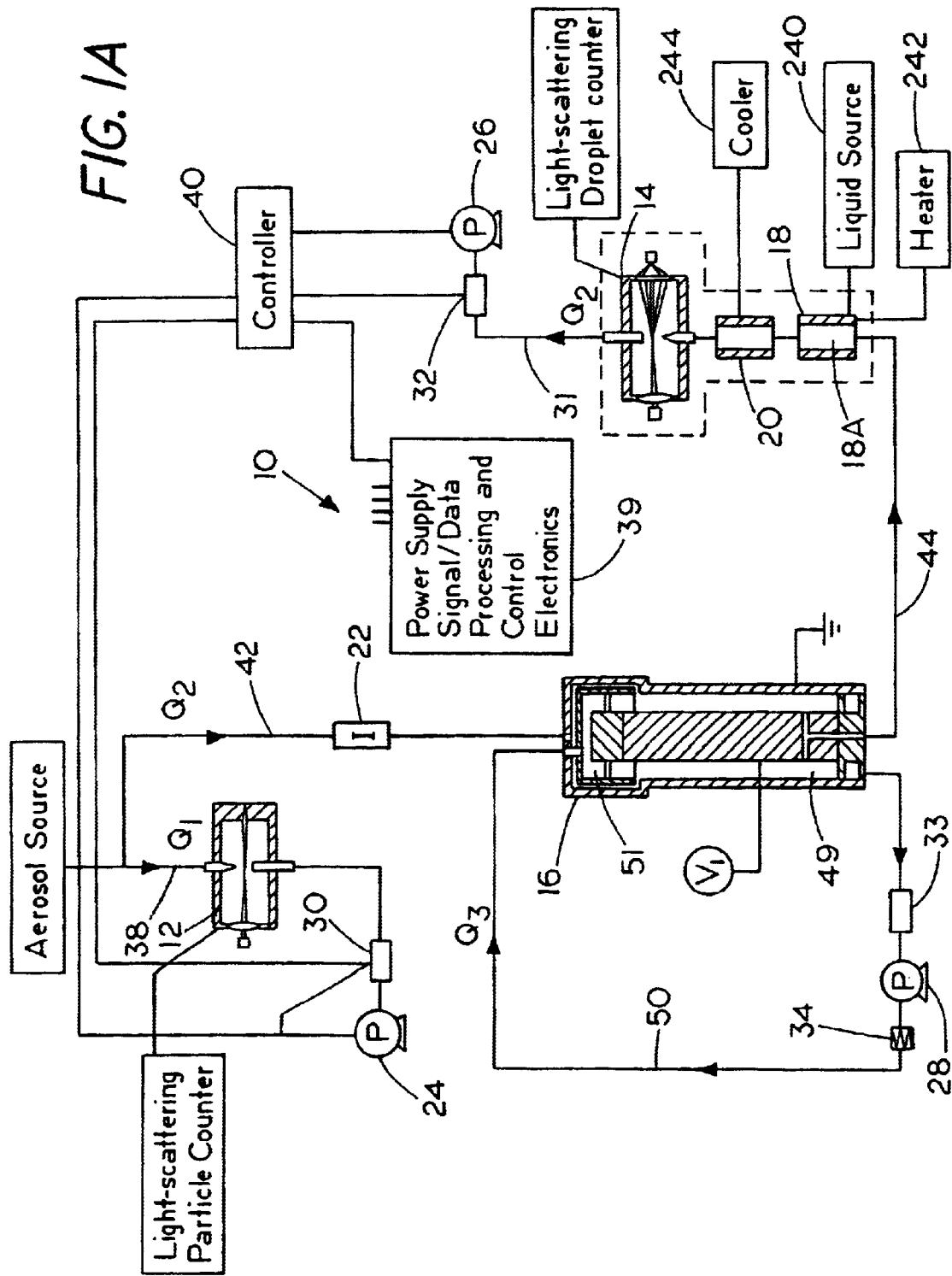
FIG. 1A is a schematic diagram of one embodiment of the present invention.

FIG. 1A is a schematic diagram of the wide range particle counter 10 in a first preferred embodiment. The particle counter 10 is on the chassis or housing 11 shown in FIG. 1. This includes two light scattering particle sensors 12 and 14, a differential mobility analyzer 16, a saturator 18, a condenser 20, an ionizer 22, and associated pumps 24, 26, 28, flow meters 30, 32 and 33, and a particle filter 34. The saturator 18 condenser 20 and light scattering particle counter 14 can be made as a sub assembly, as indicated by the dotted lines.

The first particle sensor 12 is a light-scattering particle counter (LPC) to detect coarse particles larger than a certain size, typically 300 nm in diameter. Aerosol is drawn through a line 38 from inlet tube 11C and through the LPC 12 at a flow rate of $Q_1$ liters per minute (1 pm), by the pump or flow generator 24. This aerosol airflow also passes through the flowmeter 30 to measure the flowrate of the aerosol. The output signal from flow meter 30, indicating flow rate is used in conjunction with a controller 40 to vary the speed of pump 24 to maintain a constant flow, $Q_1$, through the light scattering particle counter 12.

At the same time a second airflow, $Q_2$ is provided in a line 42 by tapping into line 38 so the same aerosol source is provided to both branches of flow. The flow in line 42 carries particles for detection below a certain limiting size, typically 300 nm in diameter, by the method of the present invention. This flow is established by pump 26. The flow $Q_2$ flows through ionizer 22, and line 42 connects to differential mobility analyzer (DMA) 16. An output line from the DMA 16 connect to a saturator 18, a condenser 20, and then to the light-scattering particle sensor 14 used as a light-scattering droplet counter (LDC). The flowmeter 32 is connected to the output or exit line 31 of the light-scattering particle sensor 14 and to pump 26. The output, of flow meter 32 is used in conjunction with an electronic controller 40 to vary the speed of the pump 26 to maintain $Q_2$ at the desired value. The electronic controller 40 can be part of an overall system 39 having a power supply, signal and data processing capabilities and control electronics. The system 39 is mounted on the chassis.

The third pump 28 connected to the sheath flow outlet of DMA 16, maintains a steady airflow, $Q_3$ in a line 50, which passes into the DMA to provide the clean sheath gas flow needed for the DMA. The flow sensor and controller needed to maintain this flow at a constant value are not shown for simplicity and clarity. The sheath flow is drawn from the annular space 49 surrounding the high voltage electrode 53. A high efficiency particle filter, 34 is used in line 50 to remove unwanted particulate contaminants in the flow $Q_3$ before it is introduced back into the DMA 16 in the sheath flow inlet chamber 51. After passing through the DMA, the sheath flow, $Q_3$, passes through a flowmeter 33, before the flow goes to the inlet of pump 28 to complete the flow loop. The output flow rate signal from flowmeter 33 is used in conjunction with electronic controller 40 to vary the speed of pump 28 to maintain the constant sheath flow, Q3.

The flow rate $Q_1$ in line 38 for the coarse particle detector or counter 12 generally must be higher than the flow rate $Q_2$, for the fine particle detector or DMA 16. For atmospheric measurements, a flow ratio of $Q_1/Q_2$ of 10 to 1 is both reasonable and quite achievable. For other applications, flow ratios of 2 to 1 or even 1 to 1 may suffice.

Due to Junge's law of atmospheric size distribution, flow ratios below 1 to 1, i.e. with $Q_1<Q_2$, would not be very useful for aerosol size distribution analysis using the multiple sensor approach described herein. In the preferred embodiment shown in FIG. 1, typical values for the flow rates are $Q_1=3$ lpm, and $Q_2=0.3$ lpm. The typical clean sheath flow rate for the DMA 16 is typically and preferably $Q_3=3$ lpm.

There is an intermediate range of particle sizes that are accurately measured by either the fine particle detector or the coarse particle detector. This intermediate size range can be from 90 nm to 600 nm. So, for a coarse particle detector that has a nominal lower limit of 200 nm the coarse detector operates into this intermediate range. The fine particle detector having an upper limit of 300 nm also operates in the intermediate range.

In addition to the embodiment of FIG. 1A, other embodiments also are usable. FIG. 2 shows a three-sensor system 59 that is mounted on the chassis 11 as shown in FIG. 1 for aerosol measurement over a 10 nm to 10,000 nm particle diameter range. In this embodiment, two light-scattering particle counters 60 and 62 are used to cover the 1,000 nm to 10,000 nm diameter range, and the 100 nm to 1,000 nm diameter range, respectively. A fine particle counter consisting of a CNC, which is shown as a light scattering droplet counter 64 receives flow from a DMA 66 through line 78, which flow passes through a saturator 68 and condenser 70, connected in a series in line 72. The fine particle counter 64 is used to cover the 10 nm to 100 nm diameter range. Again, both the fine particle counter and the coarse particle counter assembly of the two counters overlap the intermediate size range.

The input flow to the system 59 is through a line 76, carrying flow $Q_1$ from a source 77 to the input of the light scattering particle counter 60. The line 76 can be coupled to inlet tube 11C of FIG. 1. The output is connected with a line 78 through a flow meter 80, and then to an inlet side of a pump 82. The flow rate signal from the flow meter 80 is provided to a controller 84 and this signal is used to control the pump 82 so that the appropriate flow rate $Q_1$ is established in line 76. The pump 82 discharges the flow back to the atmosphere remote from the inlet of line 76. The controller 84 can be part of an overall control system 85 based on a computer for controlling the needed functions.

A line 86 is connected to line 76, and carries a particle carrying flow $Q_2$, which is lower than flow $Q_1$, provided to the counter 60. Flow $Q_2$ is provided to a second light scattering particle counter 62. The output flow from light scattering counter 62 is connected through a flow meter 88 to an inlet of a pump 90. Flow meter 88 also is connected to provide a flow signal to the controller 84 and the controller will adjust the pump 90 to establish the appropriate flow $Q_2$ in the line 86. The output of pump 90 is discharged to atmosphere, again remote from the inlet line 76.

A line 94 is connected to line 86 on an input side of the light scattering particle counter 62 and carries a flow $Q_3$ through an ionizer 96 to a differential mobility analyzer 66. The flow $Q_3$ is established by a pump 98 that is on an output side of the counter 64 and carries a flow $Q_3$ through the line 72 and an output line 100 from counter 64, through a flow meter 102 to the pump 98. The condenser 70 causes vapor generated by saturator 68A to condense on particle nuclei to form droplets that are counted by the light scattering counter 64.

The flow meter 102 also provides a signal to the controller 84 for controlling the pump 98 to provide the desired level of flow through the lines 72 and 94. The flow from pump 98 is discharged into the atmosphere.

In FIG. 2, three separate pumps, 82, 90 and 98, are shown being used with individual flow sensors and controllers to maintain the gas flow $Q_1$ $Q_2$, and $Q_3$ at their respective constant values. Another way of maintaining constant gas flows is to use critical orifices connected to a common vacuum source maintained by a single vacuum pump. When the vacuum is higher than about ½ of an atmosphere when sampling gas from atmospheric pressure, the flow becomes choked and reaches a constant value. By choosing proper orifice sizes the flows, $Q_1$ $Q_2$, and $Q_3$ can be maintained constant without separate sensors and variable speed pumps.

The sheath flow that is needed for the differential mobility analyzer is provided along a line 104, and is represented at $Q_4$. The sheath flow enters a chamber 103 in the DMA and is directed through an annular sheath flow passageway 107 and flows down around the center high voltage electrode 105.

Flow line 104 comes from an output side of a pump 106 that has an input line 108 leading from the sheath flow annular passageway 107 of the differential mobility analyzer, through a flow meter 110. A high efficiency filter 112 is in line 104 on the output side of the pump 106, so that the flow $Q_4$ is maintained very clean. The flow meter 110 also provides a signal to controller 84, for controlling the pump 106 to establish the appropriate flow rate.

The respective particle carrying flow rates for the three-sensor combination 59 are represented at $Q_1$, $Q_2$ and $Q_3$, and the flows have the relationship, $Q_1 > Q_2 > Q_3$. This particular embodiment of the invention has the advantage of further improving the statistical counting accuracy over the entire size range. At the same time the arrangement of the embodiment shown in FIG. 2 reduces the size range of particles that must be classified by the DMA 66, leading to further reduction in the high voltage required for the center electrode 105 of the DMA as will be explained, as well as the physical dimensions and weight of the DMA 66.

In yet another embodiment of particle counters assembled in the same schematic diagram as FIG. 2, the two light scattering particle counters 60 and 62 may be used to measure particles in the 5,000 nm to 50,000 nm, and 500 to 5,000 nm diameter ranges, respectively, and the DMA-CNC combination for the fine particle counter is used to measure particles in the 10 nm to 500 nm diameter range. The size range of the modified ultra-wide range particle counter (UWPC) is 10 nm to 50,000 nm, and thus even wider than that of the wide particle counter shown in the specific example of FIG. 2. The possible flow rates for the alternate form of the particle counters of FIG. 2 to form an ultra wide particle counter are: $Q_1$=30 liters per minute (lpm), $Q_2$=3 lpm, and $Q_3$=0.3 lpm. $Q_4$, the sheath flow, will remain essentially the same as in the specific form of FIG. 2.

In addition to the above, other coarse and fine particle sensors may be used in combination to overcome the fundamental limitations of the individual sensors when applied to aerosol measurement that in some cases may span nearly five decades-i.e. 2 nm to 100 nm diameter in particle size, and more than ten decades in concentration i.e. from less than 0.001 particle per cc to over $10^7$ particles per cc. A single measuring assembly having particle counting sensors as described herein makes such measurement possible.

It should be clear to those with ordinary skill in the art of particle counting that other sensor combinations, including the type and number of sensors used in the combination, may be varied to accomplish the objective of wide-range particle counting for different purposes and/or different applications without substantially deviating from the basic principle and approach of this invention.

Figure 3:
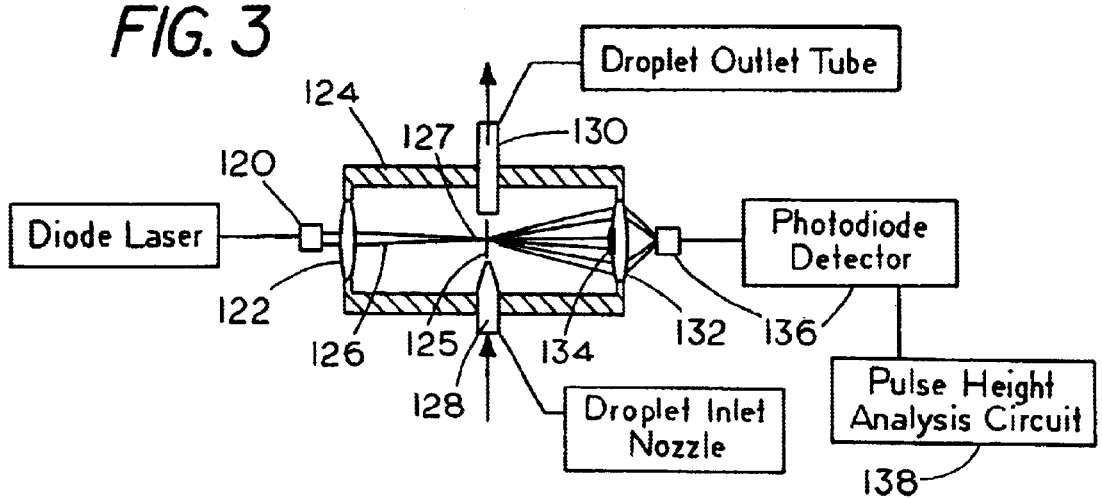
FIG. 3 is a cross-sectional view of one form of a light scattering droplet counter used with the particle counter of the present invention.
Figure 4:
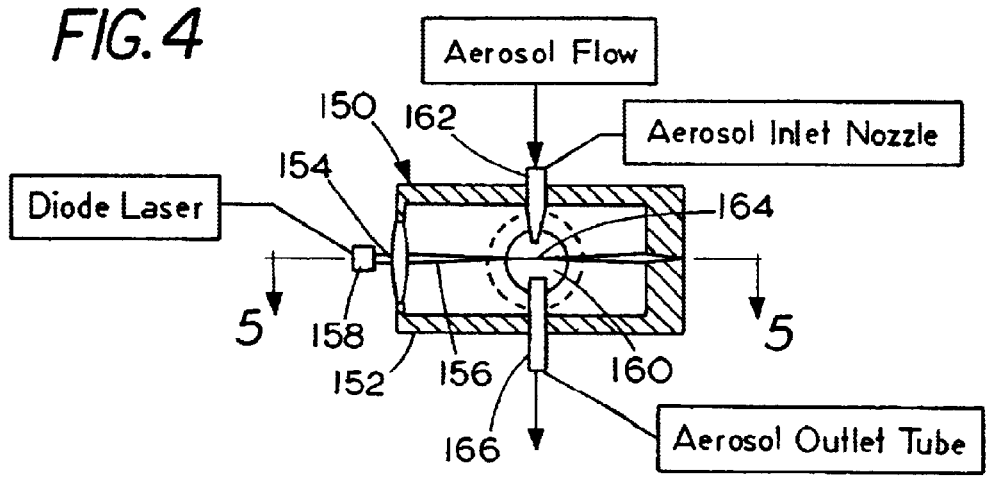
FIG. 4 is a cross-sectional view of an optical particle sensor used with the present invention using collection adapter at 90° to a laser beam.
Figure 5:
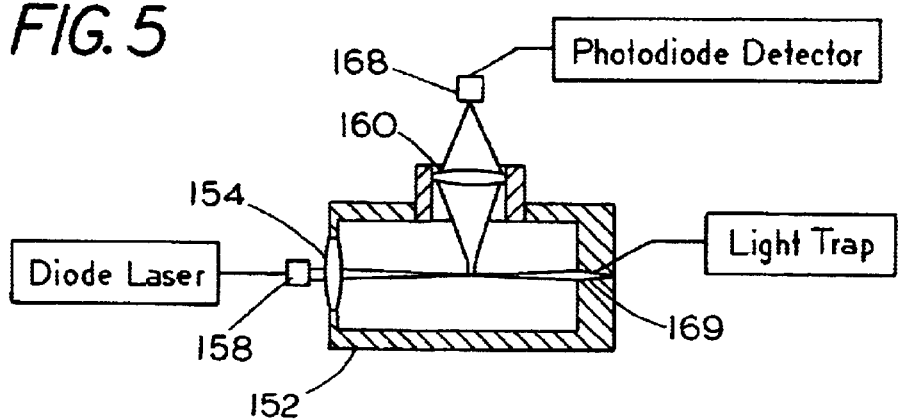
FIG. 5 is a top sectional view of the optical particle counter of FIG. 4; taken on line 5—5 in FIG. 4.

With respect to the specific optical particle counters that can be used in the wide range particle counter, FIG. 3 and FIGS. 4 and 5 show two possible designs. In FIG. 3, the optical sensor is used as a Light-Scattering Droplet Counter (LDC) for the CNC such as that shown at 14 in FIG. 1A and 64 in FIG. 2. The LDC makes use of forward-scattering optics and a solid-state diode laser 120 as the light source. The laser 120 has a suitable projection lens (not shown), to project a nearly parallel beam of collimated light through a condensing lens 122 mounted in a wall of a housing 124. Lens 122 is a cylindrical lens that brings the laser beam represented at 126 to a focus at the axis 125 of an aerosol inlet nozzle 128, and an aerosol outlet tube 130. The beam 126 widens after passing its focal point at axis 125, and projects to a lens 132 that has an opaque, light absorbing surface portion 134 that absorbs the laser beam, and thus serves as a beam stop in the center of the lens.

The aerosol is passed into the LDC housing 124 through the nozzle 128. The nozzle tapers to be smaller toward its tip and when the aerosol reaches the nozzle tip, the cross-sectional flow area is greatly reduced over the main portion of the line so the aerosol is accelerated to a high velocity. This high velocity aerosol, which is a gas containing particles to be detected, then passes through across the focused laser beam 126 and flows out of the light-scattering particle counter housing 124 through the outlet tube, 130. As each particle passes through the focused laser beam in region 127, the particle scatters light in all directions. The collecting lens 132 then collects the scattered light, within the angular range of the scattered light subtended by the lens 132 onto photodiode detector 136. A signal from photodiode 136 proportional to the light received is then processed electronically by a suitable pulse height analysis circuitry 138. Although a single lens 132 is shown as the collecting lens for the scattered-light, it is to be understood that more than one lens, or a multi-element lens, can be used as the collector to improve the performance.

FIGS. 4 and 5, an optical particle sensor 150, using 90° scattering optics is shown. The optical particle sensor 150 is used as a Light-Scattering Particle Counter such as that shown at 12, 60 and 62 in FIGS. 1A and 2 to measure the sizes of particles by sensing the scattered light signal. In sensor 150, a housing 152 mounts a cylindrical lens 154 that focuses a laser beam 156 in the housing along the axis of the beam produced by a diode laser 158. A collecting lens, 160 is mounted in a collar or tube on a sidewall of the housing 152 and will collect light scattered from particles passing across the laser beam focal point 164. The aerosol is carried into the housing 152 through an inlet nozzle 162 that narrows the aerosol to a narrow stream as it passes across the focal region or point 164 of the laser beam 156. The gas stream exits through a tube 166. The common axis of the inlet nozzle 162 and tube 166 is at 90 to the axis of collecting long 160.

The scattered-light from the particles provides light signals in the generally 90° direction from the laser beam as the particles pass through the focused laser beam. These scattered light signals are collected by the collecting lens 160, and detected by a photodiode detector 168. A conical cavity 169 in the far end wall of the housing open to receive the laser light beam 156, serves as a light trap to absorb the laser light. As each particle crosses the focus region 164 of laser beam 156, the scattered light signal from the particle is detected by the photo-diode detector, 168. It is to be noted that lens 160 is focused such that light scattering from particles passing through the focal point of the laser beam is directed to fall on the sensing surface in the photodiode detector 168.

Both the optical particle sensors with the forward scattering optics shown in FIG. 3 and the 90° scattering optics sensor of FIG. 4 and 5 can be used to detect the scattered light from particles. However, for particle sizing, it is generally preferred to use light scattering optics that excludes scattered light within a certain narrow angle in the forward direction from the optical axis of the laser beam, or in other words, scattered light that travels in the same general direction of the laser beam, or deviates only by a small angle from the direction of travel of the laser beam.

Light-scattering particle sensors with forward scattering optics that maximize the collection of scattered light signal in the forward direction are more sensitive, but give rise to a scattering signal that is not a monotonic function of particle size. The phenomenon, known as Mie resonance, can cause ambiguity in the measured particle size. For this reason, light-scattering particle sensors with 90° scattering optics (FIGS. 4 and 5), or with the optical axis of the collecting lens placed at some finite angle, such as 30°, 45°, 60°, or the like are preferred. Light-scattering particle sensors that make use of mirrors instead of lenses can also be used provided the collecting optics is designed to exclude the scattered light signal in the near forward direction of the light beam.

The airflow, $Q_2$, established by pump 26 in FIG. 1A passes through the ionizer 22, the DMA 16, the saturator 18, the condenser 20, and then the light-scattering droplet counter 14. The ionizer 22 usually contains a small, low-level radioactive source, such as radioactive Krypton 85, or polonium 210. The alpha, beta or gamma radiation emanating from the ionizing source causes air (gas) molecules to be ionized. The ionized gas molecules then collide with the aerosol particles to cause a low-level electrical charge to appear on the particles.

When the charged particles reach a state of charge equilibrium with the ions, referred to as Boltzmann equilibrium, the charged particles will bear a certain relationship to the total particles (charged and uncharged) in the gas. At Boltzmann equilibrium, particles of a specific size and carrying, say, a single electronic charge will be in a fixed ratio to the total number of particles of that size in the gas. Since this ratio is known from theory, by measuring the singly charged particles of that size, the total number of particles of that size in the gas can be determined.

Figure 6:
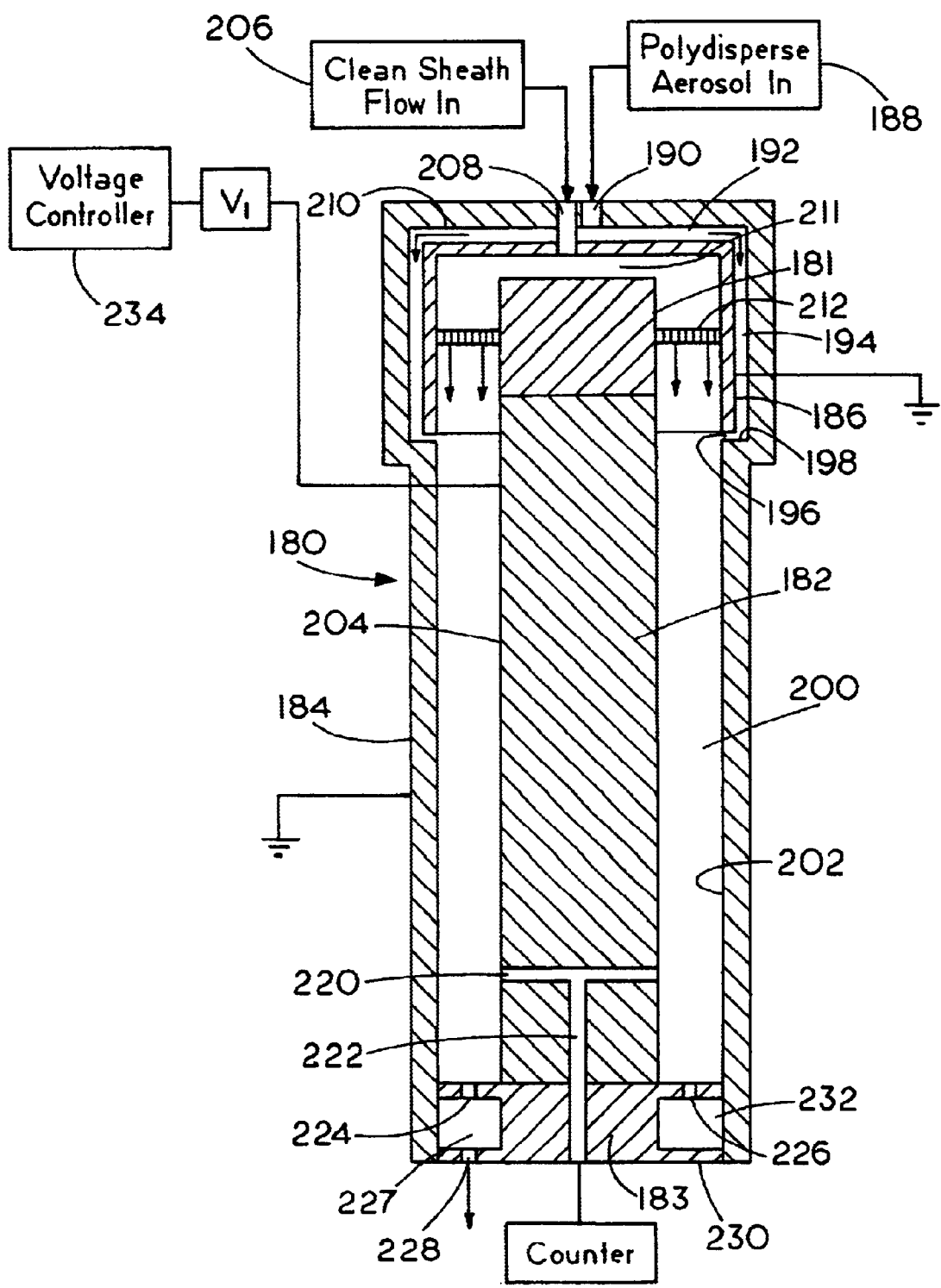
FIG. 6 is a cross-sectional view of a differential mobility analyzer used in the present invention.

There are various designs of differential mobility analyzers for aerosol classification by electrical mobility. The basic principals of operation of DMA's are well known. A schematic diagram of a preferred design for a DMA is shown in FIG. 6 at 180. It is to be understood that the DMA shown in FIG. 6 is the preferred form of the DMA's 16 and 66 in FIGS. 1A and 2. In this design a central metal cylinder 182 forming an electrode is concentratic with an outer tubular primary cylinder 184 and a shorter nested outer cylinder 186. The inner and outer cylinders 182 and 184 and 186 are at different electrical potentials chosen to establish a radial electrical field in the annular space 200 between the inner cylinder 182 and the outer cylinders 184 and 186. The inner metal electrode cylinder 182 is held at a high voltage $V_1$, while the nested outer cylinders 184 and 186 are grounded. Outer cylinders 184 and 186 have the same internal diameters so their internal surfaces form a single cylindrical surface of uniform internal diameter. The inner cylinder 182 is supported on an upper insulator support 181 and on a lower insulator support 183. Thus, the central high voltage electrode is insulated from the outer metal cylinders.

A polydisperse aerosol source 188, carrying particles in Boltzmann charge equilibrium, is introduced into the aerosol inlet 190 at the top of the DMA 180. The aerosol inlet is separate from the sheath flow inlet. This polydisburse aerosol flows radially outward in the horizontal gap space 192 forming a passage between the end walls of outer cylinders 184 and 186. The aerosol then flows through the short upper annular space 194 between short outer cylinder 186 and the upper part of primary outer cylinder 184 and emerges through the gap or space 196 between the lower end of cylinder 186 and a shoulder 198 formed on the interior of primary outer cylinder 184. The aerosol flows into an annular space 200 between the interior surface 202 of cylinder 184 and the outer surface 204 of the inner high voltage electrode cylinder 182. A radial electric field is established between surfaces 202 and 204 and is used for mobility classification.

The clean sheath gas flow needed for mobility classification, as mentioned previously, is introduced into the DMA from a source 206 through the clean sheath flow inlet tube 208 in the top wall 210 of primary outer cylinder 184. The tube 208 carries the sheath gas flow across chamber 192 and into a chamber 211 that opens to annular space 200. The sheath gas flow passes through a fine mesh screen 212 that distributes the flow evenly over the cross sectional area of the annular space 200 and establishes a laminar flow below the screen 212. As this laminar sheath gas flow merges with the laminar polydisbursed aerosol flow emerging through the slit 196, the flows combine to form a single laminar flow stream that flows down the annular space 200 between the high voltage central electrode cylinder 182 and the grounded cylinders 184 and 186.

Part of the flow in the annular space 200 can exit through a slit or a passageway 220 in the central electrode 182, that connects to an outlet bore 222 in the central electrode that opens through the insulator support 182 and leads to a particle counter. Additionally, there are a number of spaced exit holes 224 in a flange 226 of support 183. The flange 226 serves to block the annular passage 200, except for holes 224. The flow then exits out an opening 228 in an end wall 230 formed by the insulator support 183.

Particles from the polydisperse source 188 with a charge having an electrical polarity that is opposite to the polarity of the high voltage of the inner cylinder 182 are attracted to the cylinder. If the central electrode is provided with a positive polarity, the charged particles attracted to the outer surface 204 of the inner high voltage electrode cylinder 182 would be negatively charged. As the charged particles from source 188 move across and through the laminar flow in the space 200 between the cylindrical surfaces 202 and 204, the particles are classified, i.e., separated, according to electrical mobility. Small particles with high electric mobility move through the laminar sheath flow more quickly than the larger particles and the small particles are deposited on the outer surface 204 cylinder 182 above the exit slit 220. Particles that are larger than a selected size with lower mobility and moving at a lower speed, do not reach the outer surface 204 of cylinder 198. These larger particles (above the design cut off size) are carried with excess flow through the flow distributing holes 224 in the flange 226 of lower insulator support 183 into a flow plenum 227 and then exhausted through opening 228.

There is a small aerosol gas flow drawn through the exit slit 220. This flow is generated by a flow generator, as shown in FIGS. 1A and 2, pumps 26 and 98, respectively. Particles within a narrow range of electrical mobility and thus within a narrow range of size, are deflected to the vicinity of slit 220 and are carried into the outlet passage 222 as a monodisburse aerosol by the small airflow generated.

For size distribution analysis of an aerosol, the high voltage on the inner electrode 182 is adjusted through a sequence of voltage values with a voltage controller 234. At each high voltage setting, the monodisperse particles at the exit are counted by a CNC, which comprises a saturator, a condenser and a light scattering droplet counter as shown in FIGS. 1A and 2. The result can then be analyzed to give the size distribution of the aerosol.

The saturator, such as saturator 18 and 68, in a CNC usually is made of a porous material saturated with a working fluid, usually butyl alcohol in liquid form, and is shown as taken from a source 240 (in both FIGS. 1A and 2). The porous material is kept at a suitably high temperature, typically 35° C. with a heater 242. A passageway in the porous material, such as passageways 18A and 68A in FIGS. 1 and 2, allows the aerosol passing through the passageway to be heated and saturated with the vapor of the working fluid as it flows through.

The condensers 20 and 70 comprise of one or more flow passageways in a solid metal block kept at a low temperature, typically 5° C. with a cooler 244. As the heated and vapor-laden aerosol flows through the condenser 20 or 70, the gas cools, causing the vapor or gas to become supersaturated. The supersaturated vapor then condenses on the particles in the aerosol to form droplets, which are then detected by the respective light-scattering droplet counter 14 and 64. The droplets formed are larger than the particles and more easily counted.

Since the purpose of wide-range particle analysis using the WPC is to characterize an aerosol over nearly its entire particle size range, it is important that the sample drawn in by the WPC for size distribution analysis is a representative sample of the atmosphere to be analyzed. For atmospheric aerosol measurement, it is usually preferred to draw the total flow of the aerosol sample through the same common inlet, and divide this total flow into two sub-fractions, $Q_1$, and $Q_2$, for size distribution analysis by the respective coarse-particle and fine-particle detectors shown in FIG. 1A. If the atmosphere to be analyzed is the interior space of a room with uniformly distributed airborne particles, it may be permissible to draw the sample flows, $Q_1$ and $Q_2$, through separate sampling inlets for analysis by the two separate particle counters, since the atmosphere is generally uniform throughout the room.

Since the sample flow, $Q_1$ in FIG. 1A for coarse particle detection carries coarse particles up to 10,000 nm in diameter for analysis, it is preferable to make the flow passageway between the sampling inlet and particle detection zone in the coarse particle counter relatively short. In addition, it is important to design the flow passageway such as line 38 to be relatively straight, so that the sample flow undergoes little change in flow direction to avoid particle deposition in the sampling line due to particle inertia which can occur when the flow direction changes.

On the other hand, for the airflow $Q_2$, carrying particles for detection by the fine particle detector, with a typical upper particle size limit of 200 nm, there is less concern for particle loss during sampling and transport. The sampling line 42 for $Q_2$, can be relatively longer and can include one, two, or more 90-degree turns. The schematic flow diagram of FIG. 1 showing the preferred embodiment indicates how this can be accomplished. The coarse particle flow, $Q_1$, is shown to enter the coarse particle detector directly along line 38 with no substantial change in flow direction, while the fine-particle flow, $Q_2$, is sampled from the inlet with line 42 undergoes two 90 degree turns before entering the inlet of the fine particle detector, including the DMA 16.

Although the present invention has been described with reference to preferred embodiments, workers skilled in the art will recognize that changes may be made in form and detail without departing from the spirit and scope of the invention.

What is claimed is:

1. Apparatus for detecting particles in a gas over a wide particle size range, said wide particle size range having an upper limit and a lower limit, and an intermediate particle size between the limits, said apparatus including a coarse-particle detector detecting particles in a coarse particle range between the upper limit and the intermediate particle size, a fine-particle detector detecting particles in a fine-particle range between the intermediate particle size and the lower limit, and signal processing means to process electrical signals from said particle detectors, said particle detectors and signal processing means being mounted on a common chassis.

2. The apparatus of claim 1, wherein the lower limit is in a particle-size range between 2 nanometer and 20 nanometer.

3. The apparatus of claim 1, wherein the upper limit is in a particle-size range between 5,000 nanometer and 50,000 nanometer.

4. The apparatus of claim 1, wherein the intermediate particle size is in a particle-size range between 90 nanometer and 600 nanometer.

5. The apparatus of claim 1, wherein the lower limit is 10 nanometer and the upper limit is 10,000 nanometer.

6. The apparatus of claim 1 that includes a gas flow generator providing a gas flow containing particles to be detected by the coarse-particle detector and a gas flow containing particles to be detected by the fine-particle detector, wherein the volumetric rate of gas flow for the coarse-particle detector is at least as large as the volumetric rate of gas flow for the fine-particle detector.

7. The apparatus of claim 6, wherein the volumetric rate of gas flow for the coarse particle detector is at least twice the volumetric rate of gas flow for the fine-particle detector.

8. The apparatus of claim 1, wherein the coarse particle detector is an optical particle detector.

9. The apparatus of claim 8, wherein the optical particle detector includes:
 a light source for projecting a light beam through the detector;
 a light sensor sensing scattered light from the particles;
 a light collector collecting scattered light from the particles and directing the scattered light onto the light sensor.

10. The apparatus of claim 9, wherein said light collector is constructed to substantially preclude collecting scattered light within a 10° angular range around the axis of the light beam in a forward direction.

11. The apparatus of claim 1, wherein said fine-particle detector includes:
 a flow generator drawing a gas sample in a stream along a path, said sample gas containing fine particles to be detected;
 a classifier receiving the gas sample and classifying the fine particles according to electrical mobility, and providing an output flow containing particles of substantially the same electrical mobility;
 a vaporizer and condenser receiving the output flow from the classifier, the vaporizer vaporizing a working fluid in liquid form and the condenser condensing working-fluid vapor on particles in the output flow to form droplets; and
 an optical detector receiving flow from the condenser and detecting droplets formed by vapor condensing on the particles in the output flow.

12. The apparatus of claim 11, wherein the fine-particle detector further comprises an ionizer in the flow path prior to the flow entering the classifier.

13. The apparatus of claim 11, wherein the particle classifier is a differential mobility analyzer.

14. The apparatus of claim 11 including a controller connected to the flow generator for maintaining the gas flow at a desired value.

15. The apparatus of claim 14, wherein a sensor sensing flow is in the flow path and provides a signal to the controller, and the flow generator comprises a variable speed pump controlled by the controller to adjust the flow to the desired value.

16. The apparatus of claim 13, wherein a clean sheath gas flow for the differential mobility analyzer is provided from a clean gas source to a sheath gas inlet, including a variable speed pump and a sensor sensing the clean gas flow and providing a signal indicating flow rate, the variable speed pump being connected to be responsive to the signal from the flow sensor to maintain the clean sheath gas flow at the desired value.

17. The apparatus of claim 16, wherein the clean sheath gas flow for the differential mobility analyzer is drawn from the excess flow from the differential mobility analyzer, the differential mobility analyzer having an outlet for excess flow comprising flow other than flow needed to carry classified particles, the outlet being connected to the variable speed pump, a filter between the variable speed pump and the sheath gas inlet.

18. The apparatus of claim 1 further comprising a gas flow pump to maintain a gas flow containing particles to be detected by the coarse-particle detector and a gas flow pump to provide a gas flow containing particles to be detected by the fine-particle detector, wherein the gas flow for the coarse-particle detector undergoes no substantial change in flow direction before the particles. are detected.

19. An apparatus for measuring polydisperse particles over a wide size range in an aerosol flow including:
   a first optical detector receiving a first portion of the aerosol flow and detecting particles in the first portion of the aerosol flow and producing an output indicative of particle size in the first portion;
   a classifier receiving at least a second separate portion of the aerosol flow and producing an output modified aerosol flow having particles of substantially uniform electrical mobility;
   a condenser receiving the output modified aerosol flow and a working fluid and condensing vapor of the working fluid on particles classified by the classifier to form droplets in the modified aerosol flow; and
   a second optical detector receiving and detecting droplets in the modified aerosol flow from the condenser.

20. The apparatus of claim 19, wherein the first optical detector is a light-scattering optical detector.

21. The apparatus of claim 19, wherein the second optical detector is a light scattering optical detector.

22. The apparatus of claim 19, wherein the classifier is a differential mobility analyzer (DMA).

23. The apparatus of claim 22, wherein a clean gas sheath flow is obtained by directing the excess flow separated from the modified aerosol flow from the DMA through a pump and a filter to obtain the clean gas for a clean gas sheath flow.

24. The apparatus of claim 19, wherein at least one line carries the aerosol flow entering the DMA, and an ionizer in the one line to produce a mixture of particles and positive and negative ions in the aerosol flow.

25. The apparatus of claim 19, wherein there is a flow generator providing a gas controlled to maintain a gas flow at a desired value for the aerosol.

26. The apparatus of claim 25, wherein the flow generator comprises a sensor to detect the flow and provide an output and a variable speed pump to adjust the flow to the desired value in response to a sensor output.

27. An apparatus for detecting particles in a gas including a chassis, a coarse-particle detector, a fine-particle detector, and signal processing means for processing electrical signals from the detectors, said particle detectors and signal processing means being mounted on the same chassis; and means on the mounted chassis for maintaining gas flows through the coarse and fine-particle detectors, so that the volumetric rate of gas flow through the coarse-particle detector is at least as large as the volumetric rate of gas flow through the fine-particle detector.

28. The apparatus of claim 27 wherein the means for maintaining gas flow comprised a first pump for maintaining the gas flow through the coarse-particle detector at a desired value, and a second pump for maintaining a gas flow through the fine-particle detector at a desired value, and sensors to detector the gas flows through the fine-and coarse particle detectors, and the processing means including means for adjusting the speed of the pumps to maintain the gas flows at their respective desired values.

29. The apparatus of claim 27 further including an inlet to the coarse-particle detector for a gas carrying particles, a bleed line connected to the inlet for carrying a portion of the gas to the fine-particle detector, wherein the inlet comprises a line carrying flow that is substantially straight from an outer end to the coarse particle detector.

30. The apparatus of claim 27, wherein the volumetric rate of gas flow through the coarse particle detector is at least twice the volumetric rate of gas flow through the fine-particle detector.

31. The apparatus of claim 27, wherein the coarse particle detector comprises an optical particle detector.

32. The apparatus of claim 31, wherein the fine particle detector further comprises a particle classifier for classifying an aerosol according to electrical mobility, a vaporizer and condenser connected in series to vaporize a working fluid in liquid form and condense the vapor formed on particles in the flow through the fine particle detector to form droplets, and an optical droplet detector receiving flow from the condenser to count droplets in the flow.

33. The apparatus of claim 31, wherein the optical detector for coarse particles includes a light source projecting a light beam through the optical detector, a light-sensor for sensing scattered light from a particle in a selected portion of the scattered light, a light collector collecting light scattered from the particle and directing the scattered light onto the light sensor.

34. The apparatus of claim 33, wherein the fine-particle detector includes an electrical mobility based particle classifier, vaporizing and condensing means downstream of the classifier for vaporizing a working fluid in liquid form and condensing said vapor on particles in the flow through the first particle detector to form droplets, and an optical droplet detector connected to the condensing means.

35. The apparatus of claim 34, wherein the particle classifier comprises a differential mobility analyzer having a central electrode, a surrounding cylinder spaced from the central electrode to form a gas sheath flow passage, and a flow-circuit forming a clean sheath flow for the differential mobility analyzer comprising an outlet connection to the sheath flow passageway for carrying excess gas flow from the differential mobility analyzer, a filter filtering the excess flow to remove particles contained therein, and a line from the filter to return the flow back to a sheath flow inlet of the differential mobility analyzer.

36. The apparatus of claim 35, wherein the flow circuit comprises a variable speed pump to adjust the gas flow to the desired value.

37. The apparatus of claim 36 including a flow sensor in the flow circuit providing a signal indicating flow, the variable speed pump adjusting the flow in response to the flow sensor signal to maintain the flow at a desired value.

* * * * *

UNITED STATES PATENT AND TRADEMARK OFFICE
CERTIFICATE OF CORRECTION

PATENT NO. : 6,639,671 B1
DATED : October 28, 2003
INVENTOR(S) : Benjamin Y.H. Liu It is certified that error appears in the above-identified patent and that said Letters Patent is hereby corrected as shown below:

Title page,
Item [ 56], References Cited, OTHER PUBLICATIONS, "A Submicron..." reference change "Lie" to -- Liu --.

Column 4,
Line 26, after "gas" insert -- source providing source of a gas carrying particles --.
Line 28, cancel "comprises" and insert -- is connected to --.
Line 29, cancel "that is" and insert -- in a --.
Lines 29 and 30, cancel "from an outer end" and insert -- line path from the gas source --.

Signed and Sealed this

Twenty-fifth Day of October, 2005

JON W. DUDAS
*Director of the United States Patent and Trademark Office*